United States Patent
Hermansson et al.

(10) Patent No.: US 10,117,964 B2
(45) Date of Patent: Nov. 6, 2018

(54) MONOLITHIC BODIES OF SINTERED CHEMICALLY BONDED CERAMIC (CBC) BIOMATERIAL PREPARED EX VIVO FOR IMPLANTATION, PREPARATION AND USE THEREOF

(71) Applicant: DOXA AKTIEBOLAG, Uppsala (SE)

(72) Inventors: Leif Hermansson, Mölle (SE); Jesper Lööf, Bälinge (SE); Emil Abrahamsson, Huntington Beach, CA (US)

(73) Assignee: Doxa AB, Uppsala (SE)

( * ) Notice: Subject to any disclaimer, the term of this patent is extended or adjusted under 35 U.S.C. 154(b) by 0 days.

(21) Appl. No.: 15/309,848

(22) PCT Filed: May 12, 2015

(86) PCT No.: PCT/SE2015/050537
§ 371 (c)(1),
(2) Date: Nov. 9, 2016

(87) PCT Pub. No.: WO2015/174913
PCT Pub. Date: Nov. 19, 2015

(65) Prior Publication Data
US 2017/0266340 A1 Sep. 21, 2017

(30) Foreign Application Priority Data
May 14, 2014 (EP) .................... 14168318

(51) Int. Cl.
*A61L 27/10* (2006.01)
*A61L 27/12* (2006.01)
*A61K 6/00* (2006.01)
*A61K 6/02* (2006.01)
*A61K 6/06* (2006.01)
*C04B 28/06* (2006.01)
*C04B 28/18* (2006.01)
*C04B 7/32* (2006.01)
*C03C 3/091* (2006.01)
*C01F 7/16* (2006.01)
*C04B 35/195* (2006.01)
*C04B 35/111* (2006.01)
*C04B 35/14* (2006.01)
*C04B 35/48* (2006.01)
*C04B 35/488* (2006.01)
(Continued)

(52) U.S. Cl.
CPC .......... *A61L 27/105* (2013.01); *A61K 6/0073* (2013.01); *A61K 6/0082* (2013.01); *A61K 6/0088* (2013.01); *A61K 6/0205* (2013.01); *A61K 6/0631* (2013.01); *A61K 6/0643* (2013.01); *A61K 6/0662* (2013.01); *A61K 6/0675* (2013.01); *A61L 27/12* (2013.01); *C01F 7/164* (2013.01); *C03C 3/091* (2013.01); *C04B 7/32* (2013.01); *C04B 28/06* (2013.01); *C04B 28/18* (2013.01); *C04B 35/111* (2013.01); *C04B 35/14* (2013.01); *C04B 35/195* (2013.01); *C04B 35/48* (2013.01); *C04B 35/488* (2013.01); *C04B 35/624* (2013.01); *C04B 35/62665* (2013.01); *A61L 2400/18* (2013.01); *A61L 2430/02* (2013.01); *A61L 2430/12* (2013.01); *C01P 2004/51* (2013.01); *C01P 2004/61* (2013.01); *C04B 2111/00836* (2013.01); *C04B 2235/3222* (2013.01)

(58) Field of Classification Search
CPC .......... A61L 15/24; A61L 15/60; A61L 27/12; A61L 27/425; A61L 27/56; A61L 31/123; A61L 31/146; C04B 35/447; C04B 35/64; C04B 38/00; C04B 41/009; C04B 41/48; C04B 41/483; C04B 41/83
See application file for complete search history.

(56) References Cited

U.S. PATENT DOCUMENTS

| 7,494,614 B2 * | 2/2009 | Pillar ...................... A61L 15/24 264/666 |
| 2003/0121455 A1 * | 7/2003 | Hermansson ........... C04B 28/06 106/692 |
| 2009/0220566 A1 * | 9/2009 | Barralet ................ A61L 27/306 424/423 |

FOREIGN PATENT DOCUMENTS

| WO | 01/76535 A1 | 10/2001 |
| WO | 2004000241 A1 | 12/2003 |
(Continued)

OTHER PUBLICATIONS

Ni et al. Comparison of Osteoblast-Like Cell Responses to Calcium Silicate and Tricalcium Phosphate Ceramics In Vitro. J Biomed Mater Res B Appl Biomater. Jan. 2007; 80(1):174-83.*
(Continued)

*Primary Examiner* — Noah S Wiese
(74) *Attorney, Agent, or Firm* — Cantor Colburn LLP

(57) ABSTRACT

The present invention generally relates to the use of pre-formed bodies of Chemically Bonded Ceramics (CBCs) biomaterial for implantation purposes wherein the bodies are prepared ex vivo allowing process parameters to be optimized for desired long term properties of the resulting CBC biomaterial. More particularly, the pre-formed CBC material bodies of the present invention are sintered. The pre-formed body of CBC material is machined to the desired geometry and then implanted using a CBC cementation paste for fixation of the body to tissue. The invention also relates to a method of preparing pre-formed bodies of CBC biomaterial for implantation purposes, methods of preparing an implant thereof having desired geometry, and a method of implantation of the implant, as well as a kit for use in the method of implantation.

12 Claims, No Drawings

(51) Int. Cl.
    *C04B 35/624*    (2006.01)
    *C04B 35/626*    (2006.01)
    *C04B 111/00*    (2006.01)

(56) References Cited

FOREIGN PATENT DOCUMENTS

| WO | 2004/007399 A2 | 1/2004 |
| WO | 2004/037215 A1 | 5/2004 |
| WO | 2011/040851 A1 | 4/2011 |

OTHER PUBLICATIONS

Vangipuram S. Ramachandran et al.; "Significance of Low Water-Solid Ration and Temperature on te Physico-mechanical Characteristics of Hydrates of Tricalcium Aluminate"; J. Appl. Chem. Biotechnol., vol. 23; 1973; pp. 625-633.

International Preliminary Report on Patentability fir International Application No. PCT/SE2015/050537; International Application Filing Date May 12, 2015; dated Aug. 17, 2016; 10 pages International Searh Report for International Application No. PCT/SE2015/050537; International Filing Date: May 12, 2015; dated Jul. 3, 2015; 4 pages Written Opinion of the International Searching Authority for International Application No. PCT/SE2015/050537; International Filing Date: May 12, 2015; dated Jul. 3, 2015; 8 pages.

\* cited by examiner

MONOLITHIC BODIES OF SINTERED CHEMICALLY BONDED CERAMIC (CBC) BIOMATERIAL PREPARED EX VIVO FOR IMPLANTATION, PREPARATION AND USE THEREOF

CROSS-REFERENCE TO RELATED APPLICATIONS

This application is a US National Stage application of PCT/SE2015/050537 filed 12 May 2015, which claims priority to European Patent Application EP 14168318.5 filed 14 May 2014. These applications are incorporated herewith in their entireties.

TECHNICAL FIELD

The present invention generally relates to the use of pre-formed bodies of Chemically Bonded Ceramics (CBCs) biomaterial for implantation purposes wherein the bodies are prepared ex vivo allowing process parameters to be optimized for desired long term properties of the resulting CBC biomaterial. More particularly, the pre-formed CBC material bodies of the present invention are sintered. The pre-formed body of CBC material is machined to the desired geometry and then implanted using a CBC cementation paste for fixation of the sintered body to surrounding hard tissue. The invention also relates to a method of preparing pre-formed sintered bodies of CBC biomaterial for implantation purposes, methods of preparing an implant thereof having desired geometry, and a method of implantation of the implant, as well as a kit for use in the method of implantation.

STATE OF THE ART

In the art chemically bonded ceramics as biomaterials are known and have been described in a number of patent applications. A CBC material typically comprises a ceramic cement binder system and inert particles. An organic binder system may be additionally be included as a complementary binder system to the ceramic cement binder system to provide e.g. cross-linking, which occurs at an earlier stage than the hydration of the ceramic cement binder system. Such materials are especially used in dental and orthopedic applications. A number of requirements should preferably be fulfilled by such materials. The materials should i.a. be biocompatible. Properties required of the paste from which the biomaterial is formed, especially for dental applications, include good handling ability and a simple applicability in a cavity, moulding ability that permits good shaping ability, a hardening/solidification of the material that is sufficiently rapid for filling work without detrimental heat generation. After hardening, the resulting biomaterial formed should also provide serviceability directly following therapy, a high hardness and strength, corrosion resistance, adequate bonding between the hardened biomaterial and surrounding biological tissue, radio-opacity, good long-term properties and good aesthetics of the resulting hardened material.

With known CBC biomaterial systems the above desired properties cannot be optimized simultaneously. Optimisation of desired long-term properties generally negatively influences the workability and ease of application of the biomaterial, and a balance has to be struck between the desired properties.

For example, while it is known that improved mechanical strength and translucency can be obtained with a higher degree of compaction, a higher degree of compaction is known to negatively influence the workability. E.g. WO 01/76535 addresses this problem. The solution offered is to compact the powder composition into a raw compact using a reduced pressure. The resulting raw compact is then immersed into hydration liquid, and the wet raw compact is transferred to and inserted into e.g. a cavity in a tooth. An alternative solution is offered by WO 2004/000241. The solution offered is to use a higher degree of compaction and then to granulate the powder into highly compacted granules. An acceptable workability can thus be achieved. A paste can be formed from the granules and hydration liquid, which paste can thereafter be filled in a cavity.

A total system taking into account biological tissues, implant and cementation fixation of the implant of the same basic chemical system in the clinical situation while at the same time allowing for optimizing the desired long-term properties of the resulting biomaterial is still missing.

SUMMARY OF THE INVENTION

The present invention is based on the use of a pre-formed sintered body of CBC biomaterial, which is formed, e.g. by machining, into desired geometry to fit the site of implantation, such as a cavity, hydrated, and hardened ex vivo, i.e. outside the human or animal body. Thereby optimum long-term properties, notably mechanical strength and translucency can be achieved in the CBC biomaterial. According to the invention the mechanical strength and translucency is further improved by sintering of the CBC material. By means of the inventive sintering the degree of compactness can be enhanced beyond the degree of compactness obtainable merely by mechanical pressing. The open porosity can thereby also be reduced beyond the degree of compactness obtainable merely by mechanical pressing.

An implant closely matching the geometry of a cavity to be filled is formed from the preformed CBC biomaterial body, e.g. using CAD/CAM, or similar methods. Machining the preformed CBC biomaterial body to the desired geometry is preferably performed on-site (e.g. chairside) where the implantation is to be carried out.

The machined implant is then fixed or "glued" to the cavity using a CBC cementation paste.

The inventive implant and the cementation paste can be based on chemical compositions to provide a complete biomaterial system with chemistry close to that of surrounding hard tissue (enamel, dentine and cortical bone).

In a preferred embodiment the inventive ceramic cement binder system of the CBC material and cementation paste is summarized as $CaO—Al_2O_3—SiO_2—P_2O_5—H_2O$ (CASPH).

Preparing the pre-formed body of CBC biomaterial ex vivo allows for a substantial higher degree of freedom of the system and its constituents, e.g. the typically very high pH of the hydrating system does not have to be modified so as to be tolerable in vivo, and the reactivity of the hydrating system does not have to be kept reasonably low in order not to evolve too much heat so as to be tolerable in vivo, and/or in order not to harden too quickly. The pre-formed body of CBC biomaterial can thus be made using optimum pH, temperature, compaction pressure, hydration times, humidity, sintering temperature and duration, and other conditions for achieving desired properties of the hardened material. By virtue of the present invention, the workability of a paste does not have to be considered when forming the implant material. According to the present invention, any workability limitations will solely apply to the cementation paste, which is used for gluing the implant.

Additionally, the invention allows for reduced complexity of the CBC powder compositions used, and also of the hydration liquid composition used, as e.g. a complementary binder system to the ceramic cement binder system to e.g. provide cross-linking at an earlier stage than the hydration of the ceramic cement binder system, will not be required, and also acceleration of the hydration reaction will not be required. For hydration, merely pure water can typically be used according to the invention.

The invention primarily relates to dental applications, where geometry, and a similar chemistry will contribute to avoidance of tension, both mechanically and thermally, as well as to avoidance of post-operative problems.

In one aspect the present invention relates to the use of a pre-formed sintered, and hardened raw monolithic CBC material body prepared ex vivo for implantation purposes, including drug delivery.

In another aspect the present invention relates to a method of preparing ex vivo a raw, sintered monolithic body of CBC biomaterial for implantation purposes, from which body the inventive implant may be formed, comprising the following steps: A) providing a CA-, CS- or CAS-system CBC powder; B) compacting the CBC powder into a green body; S) sintering ex vivo the green body, so as to obtain a sintered body; and, D) hydrating ex vivo the sintered body obtained in step S using an aqueous hydration liquid, so as to obtain a raw sintered, hardened body of CBC biomaterial.

Machining the raw preformed CBC biomaterial body to the desired geometry can be made on the sintered, pre-formed CBC biomaterial body which is in the process of being hydrated, i.e. on a sintered, partly hydrated pre-formed CBC biomaterial body, or on the sintered, fully hydrated, and thus hardened, pre-formed CBC biomaterial body, or, provided that a sufficient pressure has been used for forming the green body, i.e. typically at least 25 MPa, on the green body of dry powder as obtained after pressing of the powder, which machined body is thereafter, sintered, and hydrated to a hardened CBC biomaterial implant.

Accordingly, in another aspect the present invention relates to a method of preparing a monolithic CBC biomaterial implant, which method is especially suited for chair-side applications, comprising the steps of: $A_{A-D}$) providing a pre-formed sintered, hardened raw monolith CBC material body for implantation purposes, obtainable by means of the above inventive method; E) establishing a desired geometry of a desired implant; and, F) machining the body of sintered, hardened monolith CBC to the desired geometry, e.g. using CAD/CAM techniques, so as to obtain a monolithic CBC biomaterial implant.

In another aspect the present invention relates to a method of preparing a sintered, monolithic CBC biomaterial implant ex vivo comprising the following steps: A) providing a CA-, CS- or CAS-system CBC powder; B) compacting the powder into a green body; S sintering ex vivo the green body, so as to obtain a sintered body; D) hydrating ex vivo the sintered body obtained in step S, optionally after machining thereof in step F, using an aqueous hydration liquid, so as to obtain a sintered, hardened body of CBC biomaterial; E) establishing a desired geometry of a desired implant; and, F) machining to the desired geometry, e.g. using CAD/CAM techniques, either: a) the compacted dry powder green body obtained in step B; b) the partly or fully hydrated body in step D, or; c) the sintered body obtained in step S, so as to obtain a monolithic CBC biomaterial implant.

In a further aspect the present invention relates to a sintered, pre-formed hardened raw monolithic CBC material body having an open porosity within the range of 2-8% and improved mechanical strength.

In yet an aspect the invention relates to an implant having a desired geometry, and having an open porosity within the range of 2-8% and improved mechanical strength, which implant can be formed from the sintered, pre-formed hardened raw monolithic CBC material body prepared ex vivo, which implant is obtainable using methods of the invention.

In another aspect the present invention relates to a method of implanting a monolithic sintered CBC biomaterial implant prepared ex vivo comprising the steps of: $A_{A-F}$) providing a machined monolithic, hardened, sintered, CBC biomaterial implant, obtainable by means of the corresponding inventive method set out above; G) providing a CA-, CS- or CAS-system CBC powder; I) mixing the CBC powder with an aqueous hydration liquid, so as to obtain a cementation paste; J) applying the paste obtained in step I to the implant; K) inserting the implant with the paste applied thereupon obtained in step J into the site of implantation; and, L) allowing the paste to harden at the site of implantation in vivo for fixation of the implant to the surrounding endogenous hard tissue.

In yet another aspect the present invention relates to a kit for use in the implantation method comprising a preformed hardened, sintered, raw monolithic CBC material body for implantation purposes; and a specified quantity of CBC powder, and a corresponding quantity of hydration liquid forming a cementation paste with the CBC powder upon mixing therewith.

In preferred embodiments of the inventive implantation method and kit, the CBC powder and aqueous hydration liquid will be selected so as to form a cementation paste belonging to the CASPH-system.

Further aspects, advantages and embodiments will be apparent from the following detailed description and appended claims.

Definitions

The term "CA-system" is used herein to denote a ceramic cement binder system based on any phases of calcium aluminate ($CaO$—$Al_2O_3$).

The term "CS-system" is used herein to denote a ceramic cement binder system based on any phases of calcium silicate ($CaO$—$SiO_2$).

The term "CAS-system" is used herein to denote a ceramic cement binder system containing phases of both calcium aluminate ($CaO$—$Al_2O_3$) and calcium silicate ($CaO$—$SiO_2$), which system is based on either one of, or a combination of, calcium aluminate and calcium silicate.

The term "CASP-system" is used herein to denote a ceramic cement binder system containing phases of calcium aluminate ($CaO$—$Al_2O_3$) and calcium silicate ($CaO$—$SiO_2$), which system is based on either one of or both of calcium aluminate and calcium silicate, additionally containing phases of calcium phosphate ($CaO$—$P_2O_5$), which system may be summarized as $CaO$—$Al_2O_3$—$SiO_2$—$P_2O_5$.

The term "CASPH-system" is used herein to denote a CASP-system additionally containing water, which system may be summarized as $CaO$—$Al_2O_3$—$SiO_2$—$P_2O_5$—$H_2O$.

The term "CAH-system" is used herein to denote a CA-system additionally containing water, e.g. a fully hydrated CA-system.

The term "CBC powder" is used herein to denote the complete powder composition forming the CBC upon hydration thereof, which powder comprises the ceramic cement binder system, and inert particles, and, optionally, any additives.

The term "sintered body" is used herein to denote a body with a compaction degree after sintering with an open porosity in the interval of 10-25 vol-% before hydration thereof. Subsequent hydration will further reduce the porosity.

DETAILED DESCRIPTION OF THE INVENTION

The present invention is based on a unique utilization of a nanostructural chemically bonded ceramic system comprising both a pre-sintered material (the implant) with low porosity before hydration, e.g. as an inlay or onlay prepared to the final geometry by CAD/CAM or similar on-site (e.g. chairside) methods, and a cementation system for fixation of the preformed implant. The implant and the cementation paste may be based on similar chemistry to provide a complete biomaterial system with chemistry close to that of hard tissue (enamel, dentine and cortical bone). Such system is summarized as $CaO$—$Al_2O_3$—$SiO_2$—$P_2O_5$—$H_2O$ (CASPH).

These findings in the first place relate to dental applications to allow for a low porosity, where geometry, similar chemistry contribute to avoidance of tension mechanically and thermally, as well as avoidance of post-operative problems are of great importance.

The present invention will allow for an improved translucency to be obtained in the CBC material, by virtue of being formed ex vivo, and especially by virtue of the inventive sintering step. Also, since higher pressure can be used for compaction, translucency can be obtained with less complex compositions, as compared to the compositions used for giving high translucency in materials from a paste.

The present invention also allows for the generally preferred calcium aluminate, not just the $CaOxAl_2O_3$ phase (CA), but also the $3CaOxAl_2O_3$ phase ($C_3A$) to be used, which is otherwise typically considered too reactive to be used in vivo. During hydration of the $C_3A$-phase only the hydrated phase $C_3AH_6$ is formed, no complementary phase. Also, the reaction of heat associated with the use of $C_3A$ may often be limiting to its applicability. Other suitable phases in the calcium aluminate system are the $12CaOx7Al_2O_3$ phase ($C_{12}A_7$) or mixtures of calcium aluminate phases, crystalline and/or in glass/amorphous state.

The inventive biomaterial system is based on chemically bonded ceramics, wherein the ceramic phase is based on Ca-aluminate and/or Ca-silicate.

The present invention is based on findings related to a specific chemical system based on materials produced from the $CaO$—$Al_2O_3$—$SiO_2$—$P_2O_5$—$H_2O$ (CASPH)-system. The CASPH-system is close in chemistry to that of body hard tissues such as enamel, dentine and different bone structures. The complete system comprises 4 aspects which all are essential. These aspects relate to 1) a premade implant, 2) configuration of the implant, 3) in situ preparation of the final geometry in the clinical situation, and 4) cementation of the implant.

The premade implant is prepared outside the body to yield a high strength, low-porosity implant. The formation of the premade implant takes into account the following aspects; a) the possibility of using a temperature above body temperature for the hydration, b) the possibility of pressing of the original powder to a high density, c) possibility of hydrating the material using merely pure water as hydration liquid, d) possibility of using CBC powder composition of reduced complexity, e) inclusion of a sintering step, and f) achievement of an acid resistant material, as well as achievement of g) highly bioactive materials having improved translucency.

The invention generally relates to dental materials and implant materials used in hard tissue. The invention is aimed at producing biomaterials for dental applications with special reference to dental filling materials including underfillings and sealants, and general bone void filling.

A second binder system—a cross-linking organic binder system which provides for initial crosslinking of the freshly mixed paste—can be included in the cementation paste. Such systems are known in the art.

The invention is described in more detail below with special reference to development of the selected chemical system, the pre-formed CBC biomaterial body using presintering and methods to prepare the final geometry of the implant.

The Chemically Bonded Ceramic System of the Pre-Formed Sintered Body.

The ceramic cement binder system of the chemically bonded ceramic system of the invention is based on calcium aluminate (e.g. CA, $C_3A$) and/or calcium silicate (e.g. CS) phases, i.e. the ceramic cement binder system is a CA-, CS-, or CAS-system. The ceramic cement binder system is capable of being hydrated. In a preferred embodiment the ceramic cement binder system of the chemically bonded ceramic system of the invention is based on calcium aluminate (i.e. a CA-system), and the preferred phases are $C_3A$ and CA, especially $C_3A$. The mean particle size of any particles present in the original powdered material should be below 10 μm, and the amounts of the chemically bonded Ca-aluminate phases should correspond to a c/w ratio close to complete conversion, the latter favoring general low porosity in the microstructure, comprising mainly of nanostructures including nanoporosity.

Lower contents of phases from the $CaO$—$SiO_2$—$H_2O$ system and/or $CaO$—$P_2O_5$—$H_2O$ system are also preferred, especially from the $CaO$—$P_2O_5$—$H_2O$ system to facilitate formation of apatite phases.

Accordingly, in a preferred embodiment the ceramic cement binder system of the pre-formed implant is a CASPH-system, preferably based on calcium aluminate, the preferred phases of which are $C_3A$ and CA, especially $C_3A$.

In a preferred embodiment the raw sintered monolithic body of CBC biomaterial, from which the inventive implant is formed, is prepared using a CA-, CS- or CAS-system CBC powder comprising the phase $C_3A$.

The binder system preferably constitutes 15-45% by weight of the CBC powder.

An especially preferred CBC powder for preparing the monolithic sintered body comprises 15-45% by weight of the ceramic cement binder system wherein the calcium aluminate phase $C_3A$ constitutes at least 15% by weight of the CBC powder, and 55-85% by weight of inert particles having an average particle size of <10 μm. Other phases of calcium aluminate ($CaO$—$Al_2O_3$), and, optionally, any phases of calcium silicate ($CaO$—$SiO_2$), may also be present in the CBC powder. Preferably the cement binder system is based on calcium aluminate, and more preferably the phase $C_3A$. In a preferred embodiment $C_3A$ is the sole phase of the cement binder system.

Compaction of the CBC Powder

The powder is compacted using any traditional pressing techniques, including general pressing and isostatic pressing. The pressing technique is preferably selected so as to give the compacted material a high density. The total porosity is favorably below 45 vol-%, preferably in the interval 30-40% depending on the exact selected composition of the material. In order for the green body resulting from compaction of the powder to allow for machining thereof, the pressure used should be at least 25 MPa, e.g. within the interval of 50-350 MPa, preferably about 100 to about 300 MPa, typically from 100 MPa to 280 MPa.

Sintering of the Green Body

Sintering of the pre-compacted body is used as an additional compaction of the green body. The sintering provides the body, after sintering thereof, with a porosity in the interval of 10-25 vol-%. The prepressed green body is sintered at a temperature in the interval of from 1,200-1,500° C. for a time period in the interval of about 15 minutes to several hours. For $C_3A$ the preferred interval is 1,275-1,375° C. for a time period in the interval of 1-2 hours.

The subsequent hydration will further reduce the porosity of the sintered body to a porosity within the interval of 2-8 vol-%, preferably below 7 vol-%, and more preferably below 4 vol-%. The porosity, which after hydration will take the form of nanopores, remains open.

Forms and Sizes of the Pre-formed Sintered Raw Body

Suitable dimensions of individual pre-formed sintered raw bodies are e.g. in the interval of 3-12 mm. A suitable shape is e.g. rods, tablets, or platelets. The preformed bodies can be provided with notches, or portions with otherwise markedly reduced cross-sectional area, so that individual bodies easily can be broken off from a larger body.

Hydration Temperature.

The premade implant is hydrated outside the body allowing hydration temperatures above body temperature. The preferred hydration temperature is within the interval of 50-90° C.

The Hydration Liquid

The bulk of the liquid used is water. For the pre-made implant pure water is preferred.

The Nanostructure.

The inventive requirements of the microstructure of Ca-aluminate and/or Ca-silicate based biomaterials allow the total biomaterial to be on the nanoscale level after hydration. This refers both to the premade biomaterial and the cementation paste by:

a) the general nanostructure developed in the CASP-system;
b) a nanoparticle/crystal size of hydrates in the interval 15-40 nm;
c) a nanoporosity size of 1-4 nm; and,
d) original particle size of the reacting chemically bonded ceramics of <10 μm.

The use of a premade sintered implant according to the described conditions will guarantee that the nanostructure also will:

a) be free of large pores from handling aspects; and
b) exhibit a low content of nanopores, preferably below 7 vol-%, most preferably below 4% upon hydration thereof.

The Inert Filler Particles in the Premade Implant

A complementary inert filler material in the premade implant is preferably used to enable complete hydration of the ceramic cement binder system. The inert filler material can be a hydrated CBC biomaterial, e.g. having same composition as the inventive CBC biomaterial, or e.g. a glass. A preferred inert filler is a glass with a refractive index close to that of the hydrated phases, i.e. a refractive index in the interval 1.58-1.67. The resulting reduced porosity of the sintered body will allow for accommodation of less water into the system for hydration of the binder phase. To compensate for the lower amount of water available for hydration of the binder phase, the content of the inert filler system is preferably increased, and is preferably in the range of 55-85 w/o, more preferably 70-80 w/o, of the CBC powder to provide conditions for complete hydration of the ceramic cement binder system.

The Cementation Paste

The cementation cement or paste is preferably based on the system $CaO-Al_2O_3-SiO_2-P_2O_5-H_2O$ (CASPH). The ceramic cement binder system of the cementation paste will thereby exhibit a chemistry close to both the chemistry of the premade implant, e.g. the CAH system, and the chemistry of hard tissue, which is mainly a Ca-phosphate system. For optimum rheological and handling aspects a glass ionomer system may be added. The CBC powder used for preparing the cementation paste is preferably based upon mono-phase CA. A suitable amount of the glass ionomer when used is for example about 15% by weight of the CBC powder.

The Clinical and the In-situ Preparation

The premade implant is given its final geometry using in the clinic present CAD/CAM equipment or similar equipment on-site (e.g. chairside), or at general dental laboratory CAD/CAM equipment or similar equipment. The final cementation (the paste) is prepared in minutes just before treatment and the bond between the final implant and the tissue is established in minutes after treatment.

Machining the preformed CBC biomaterial body to the desired geometry can be made on the green body of dry powder as obtained after pressing of the powder, which body after machining thereof is sintered and hydrated to a hardened, sintered CBC biomaterial implant, on the sintered body as obtained after sintering, or on the pre-formed, sintered CBC biomaterial body which is in the process of being hydrated, i.e. on a partly hydrated pre-formed CBC biomaterial body, or on the fully hydrated, and thus hardened, pre-formed CBC biomaterial body. Machining the green body of dry powder, or the partly hydrated pre-formed body will allow for greater ease of machining. However, for clinical chairside applications the premade implant will typically be provided in a sintered and hydrated form, which will merely be machined at the clinic to the appropriate geometry.

The present invention is preferably used as inlays, tooth fillings including underfillings, and fissure sealings. Other application fields according to the present invention are within orthopedics, and as a carrier for drug delivery.

The Kit

The present invention also relates to a kit for use in the implantation method comprising a preformed hardened, sintered, raw monolithic CBC material body for implantation purposes; and a specified quantity of CBC powder, and a corresponding quantity of hydration liquid for forming a cementation paste thereof.

In preferred embodiments of the inventive implantation method and kit, the CBC powder and aqueous hydration liquid will be selected so as to form a cementation paste belonging to the CASPH-system.

The kit is preferably in the form of a capsule or syringe mixing system containing the CBC powder and the aqueous hydration liquid in separate capsules or syringes, respectively.

EXAMPLES

Description of Raw Materials and Preparation
1. The calcium aluminate ($C_3A=3(CaO)(Al_2O_3)$) used was synthesised and treated according to the description below.
2. Deionised water.
3. Inert glass of the composition $SiO_2$—$BaO$—$B_2O_3$—$Al_2O_3$ in wt % 50-30-10-10 average particle size 0.4 µm, $d(99) \leq 3$ µm.
4. LiCl as an accelerator for the cement paste hydration was used as a pre-prepared standard solution, p.a. quality.

Example 1

Preparation of the Powder and Pressed Rods/Tablets

The calcium aluminate used for this material was synthesized using high purity $Al_2O_3$ and $CaCO_3$. The appropriate amounts of the raw materials are weighed in to a suitable container (1:3 molar ratio). The powders are intimately mixed by tumbling in excess isopropanol. Thereafter, the isopropanol is removed, such as by evaporation of the solvent using an evaporator combining vacuum and heat and finally heating in oven. The next step is filling high purity $Al_2O_3$ crucibles with the powder mix and heat treating it at a temperature of 1,340° C. for 4 h. After heat treatment the material is crushed using a high energy crusher, in this case a roller crusher with alumina rollers. After crushing the calcium aluminate is milled using an air jet mill (Hosokawa Alpine) to the specified particle size distribution with a $d(99)v$ of <8 µm and an average particle size of 3 µm.

The final powder formulation is obtained in the following way: All powder components are weighed in with high accuracy according to the composition in Table 1.

TABLE 1

Composition of the final powder formulation for the implant.

| Raw material | Wt % |
|---|---|
| Calcium aluminate $C_3A$ phase | 22.00 |
| Glass, inert Ps < 0.5 µm | 78.00 |

The components are weighed into a glass beaker, and the beaker is thereafter placed in a dry mixer and the components are mixed for 3 hours. The next step after mixing is sieving through a 125 µm sieve in order to homogenize the powder and remove large agglomerates. After sieving, the powder is transferred to a suitable container, which is then sealed and stored dry. The powder is pressed into rods (diameter 8 mm and length 8 mm.).

The powder was pressed into rods using cold isostatic pressing. The cold isostatic pressing was performed at 100 MPa.

Example 2

Sintering of the Pressed Rods

The rods prepared in Example 1 above were thereafter sintered at a temperature of 1,280° C. for different time periods (15 min to 12 hrs), yielding a further compaction of the bodies, corresponding to a total porosity prior to hydration of maximum 25 vol-%, as set out in the Table below.

Example 3

Machining into Desired Geometry

The final geometry was accomplished by means of machining the sintered body obtained in Example 2 using CAD/CAM.

Example 4

Hydration of the Sintered Bodies

The liquid for hydration was prepared as follows. The $Ca_3(PO_4)_2$ is added to pure, deionized water in an amount of 2% by weight. The liquid is now ready for use as a hydration liquid for hydrating the preformed sintered body.

Using the above hydration liquid the sintered bodies obtained in Example 3 above were hydrated in a closed chamber at 60° C. for 4 hours. The humidity in the chamber was close to 100%.

The hydrated, sintered bodies having a final geometry are now ready to be implanted using the below described cementation paste as a glue for fixation thereof to tissue. See Example 5 below.

Example 5

Preparation of the Cementation Paste

The CBC powder used in this Example is based on the mono-phase $CaO\,Al_2O_3$ (CA) and comprises 15% by weight of a glass ionomer. The powder is mixed by hand with a sufficient amount (about 45 vol-% of the total paste thus formed) of the hydration liquid described in Example 4 to form a paste. The paste may in a next step be used to glue the pre-prepared sintered hydrated body to tissue.

Example 6

Description of Tests and Results Obtained

The premade sintered and hydrated implants prepared above were evaluated chemically, mechanically and biologically according to the table below. Each test comprised 12 samples. The tests were conducted using standard ISO testing, which comprises the following sections: Cytotoxicity (ISO10993-5), Sensitization (ISO10993-10), Irritation/Intracutaneous reactivity (ISO10993-10), Systemic toxicity (ISO10993-11), Sub-acute, sub-chronic and chronic toxicity (ISO10993-11), Genotoxicity (ISO10993-3), and Implantation (ISO10993-6).

The porosity of the sintered bodies was calculated by use of the density of compounds of the body and the volume of the sintered body. The porosity of the sintered and hydrated bodies were measured by weighing the material before and after hydration, respectively, and by measuring the reduction of weight after drying the hydrated bodies at a temperature of 125° C. for 2 hrs.

| Duration of sintering | Porosity after sintering | Porosity after hydration | Compression strength | Biocompatibility | Bioactivity | Translucency % |
|---|---|---|---|---|---|---|
| 15 min | 25% | 7% | 250 ± 12 | OK | OK | 30 ± 2 |
| 4 hrs | 17% | 4% | 380 ± 8 | OK | OK | 38 ± 3 |
| 12 hrs | 14% | 3% | 390 ± 8 | OK | OK | 42 ± 3 |

The invention claimed is:

1. A method of preparing ex vivo a monolithic sintered, hardened raw body of CBC biomaterial for implantation purposes comprising the following steps:
   A providing a CA-system CBC powder or a CAS-system CBC powder additionally containing phases of calcium phosphate;
   B compacting the CBC powder into a green body;
   S sintering ex vivo the green body, so as to obtain a sintered body; and
   D hydrating ex vivo the sintered body obtained in step S using an aqueous hydration liquid, so as to obtain a raw hardened, sintered body of CBC biomaterial.

2. The method of claim 1, wherein the CBC powder is a CAS-system CBC powder additionally containing phases of calcium phosphate.

3. The method of claim 1, wherein the CBC powder is a CA-system CBC powder.

4. The method of claim 1, wherein the predominant Ca-aluminate phase is $C_3A$.

5. A method of preparing ex vivo a sintered, monolithic CBC biomaterial implant comprising the following steps:
   A providing a CA-system CBC powder or a CAS-system CBC powder additionally containing phases of calcium phosphate;
   B compacting the powder into a green body;
   S sintering ex vivo the green body, so as to obtain a sintered body;
   D hydrating ex vivo the sintered body obtained in step S using an aqueous hydration liquid, so as to obtain a hardened, sintered body of CBC biomaterial;
   E establishing a desired geometry of a desired implant;
   F machining to the desired geometry established in step E either:
      a) the compacted dry powder green body obtained in step B;
      b) the partly or fully hydrated body in step D; or
      c) the sintered body obtained in step S, so as to obtain a monolithic CBC biomaterial implant.

6. The method of claim 5, wherein the CBC powder is a CAS-system CBC powder additionally containing phases of calcium phosphate.

7. The method of claim 5, wherein the CBC powder is a CA-system CBC powder.

8. The method of claim 5, wherein the predominant Ca-aluminate phase is $C_3A$.

9. A method of preparing ex vivo a monolithic, sintered CBC biomaterial implant, especially suited for chairside applications, comprising the steps of:
   $A_{A-D}$ providing a pre-formed hardened, sintered raw monolithic CBC material body for implantation purposes, obtained by the method of claim 1;
   E establishing a desired geometry of a desired implant; and,
   F machining the pre-formed hardened, sintered raw monolithic CBC material body to the desired geometry established in step E so as to obtain a monolithic CBC biomaterial implant.

10. The method of claim 5, wherein machining step (F) is accomplished using CAD/CAM.

11. The method of claim 9, wherein machining step (F) is accomplished using CAD/CAM.

12. A method of implanting a hardened, sintered, monolithic CBC biomaterial implant prepared ex vivo comprising the steps of:
   $A_{A-F}$ providing a machined monolithic, sintered, hardened CBC biomaterial implant, obtained by the method of claim 5;
   G providing a CA-, CS- or CAS-system CBC powder;
   I mixing the CBC powder with an aqueous hydration liquid so as to obtain a cementation paste;
   J applying the paste obtained in step I to the implant;
   K inserting the implant with the paste applied thereupon obtained in step J into a site of implantation; and
   L allowing the cementation paste to harden at the site of implantation in vivo for fixation of the implant to the surrounding endogenous hard tissue.

* * * * *